United States Patent [19]

Moreno

[11] Patent Number: 5,781,274

[45] Date of Patent: Jul. 14, 1998

[54] DEVICE FOR EXERCISING THE CILIARY MUSCLE

[76] Inventor: Gil G. Moreno, 4106 Dellbrook Dr., Tampa, Fla. 33624

[21] Appl. No.: 897,497

[22] Filed: Jun. 18, 1997

[51] Int. Cl.$^6$ ............................................. A61B 3/00
[52] U.S. Cl. ........................................ 351/203; 351/221
[58] Field of Search ................................. 351/203, 221, 351/200, 205, 201, 246

[56] References Cited

U.S. PATENT DOCUMENTS

| | | | |
|---|---|---|---|
| 3,774,599 | 11/1973 | Martin | 128/76.5 |
| 3,843,240 | 10/1974 | Cornsweet | 351/2 |
| 3,875,934 | 4/1975 | Sadanaga | 128/76.5 |
| 4,402,580 | 9/1983 | Ross | 351/203 |
| 4,408,846 | 10/1983 | Balliet | 351/203 |
| 4,464,027 | 8/1984 | Cooper | 351/203 |
| 4,506,963 | 3/1985 | Cooper | 351/203 |
| 4,838,677 | 6/1989 | Bronskill | 351/203 |
| 4,854,690 | 8/1989 | Mehr | 351/203 |
| 4,940,323 | 7/1990 | Downing | 351/203 |
| 5,040,888 | 8/1991 | Bonham | 351/203 |
| 5,422,688 | 6/1995 | Asea | 351/203 |
| 5,520,543 | 5/1996 | Mitui | 434/236 |

OTHER PUBLICATIONS

U.S. application No. 08/722,555, Moreno, filed Sep. 27, 1996.

Primary Examiner—Hung X. Dang

[57] ABSTRACT

This relates to a device to be located in front of one eye or both, eyes to exercise the ciliary muscle. A plurality of light sources are disposed and mounted on the inner surface of a first tubular enclosure. Said first tubular enclosure has one end open, and the other end is closed. In a first preferred embodiment said open end is of sufficient amplitude to be located in front of only one eye at a time. In a second preferred embodiment said open end is of sufficient amplitude to be able to be located in front of both eyes. Said light sources are located at different distances from the open end of said first tubular enclosure. Said light sources are turned on and off sequentially. The sequence may be away or toward said open end, random or any other desired pattern.

11 Claims, 5 Drawing Sheets

DEVICE FOR EXERCISING THE CILIARY MUSCLE

The mechanism by which the eye is able to see objects without blur at various distances is known as accommodation. The accommodation in human eye is accomplished by a change in curvature of the crystalline lens by the action of the ciliary muscle and the zonule.

The closest point that the eye can accommodate is defined as the near point of accommodation. The near point of accommodation of a child ten year old with normal vision is approximately seven centimeters. When the child grows older, he focuses his eyes on objects not closer than thirty centimeters. This continues for the rest of his life. As a consequence, the ciliary muscle is not exercised in the range from approximately seven centimeters to approximately thirty centimeters. Intuition indicates that this situation can create a partial atrophy of the ciliary muscle and zonule. Therefore, exercising the ciliary muscle and zonule from approximately seven centimeters to approximately thirty centimeters could be of great benefits.

U.S. Pat. Nos. 4,838,677 and 3,875,934 teach complicated electromechanical devices for exercising the ciliary muscle.

No practical device is known for exercising the ciliary muscle that is portable, effective, light weight, and that requires minimum mental effort during its use.

SUMMARY OF THE INVENTION

The principal object of the present invention is to provide a device to exercise the ciliary muscle that is portable, effective, lightweight, and that requires minimum mental effort during its use.

It is also an object of the present invention to provide a device which is of inexpensive construction.

Another object of the present invention is to provide a device that is attractive and pleasant to use.

A further object is to provide a device which will contribute to a healthy vision.

For accomplishing this objects, a plurality of light sources are disposed and mounted on the inner surface of a first tubular enclosure. Said first tubular enclosure has one end open and the other end is closed. Said plurality of light sources are aimed to the open end, and are located at different distances from the open end of said first tubular enclosure. Each individual light source is turned on and off sequentially. When a light source turns off, the following light source turns on immediately or after a predetermined time delay. The sequence may be away from the open end of said first tubular enclosure, toward the open end of said first tubular enclosure, random or any desired pattern. Said light sources may have a transparent film with black figures, or a black film with cut out figures to modulate the light beam emitted. A second tubular enclosure surrounds said first tubular enclosure providing an space between them. A case containing an electronic circuitry to control said light sources and an electric battery is attached to the close end of said first tubular enclosure or to said second tubular enclosure. The space between said first and second tubular enclosures is used as a raceway for electrical conductors. The cross section of said first and second tubular enclosures may be circular, elliptical, or any desired shape. The amplitude of the cross section of said first and second tubular enclosures may be uniform, or it may diminishes from the open end to the close end. The person using this device must fixate the light source that turns on sequentially.

In a first embodiment of the present invention, the open end of said first tubular enclosure is of sufficient amplitude to be located in front of only one eye, that is to be exercised, while the other eye remains at rest. The device further includes a shield to prevent external light from entering the resting eye.

In a second embodiment of the present invention, the open end of said first tubular enclosure is of sufficient amplitude to be able to be located in front of both eyes to be exercised simultaneously or one at a time. The device has two movable shields able to be positioned to cover one eye at a time while the other eye is being exercised. The device further has the edge of the open end of said first tubular enclosure shaped to conform with forehead and chin contours, or may be provided with adjustable forehead and chin supports. Some of the light sources may be located adjacent the edge of of the open end of said first tubular enclosure and turned on and off sequentially in a clock-wise direction, counter clock-wise direction or any other pattern, to exercise the extraocular muscles.

DESCRIPTION OF THE PREFERRED EMBODIMENTS

A first preferred embodiment

Figure 1:
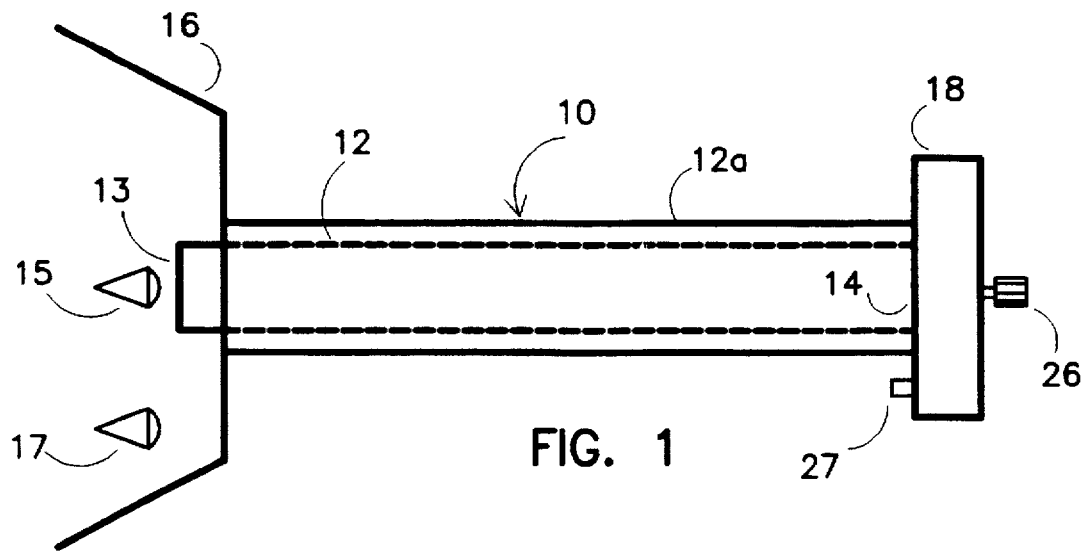
FIG. 1 is a top view of the device for exercising the ciliary muscle of one eye at a time.
Figure 2:
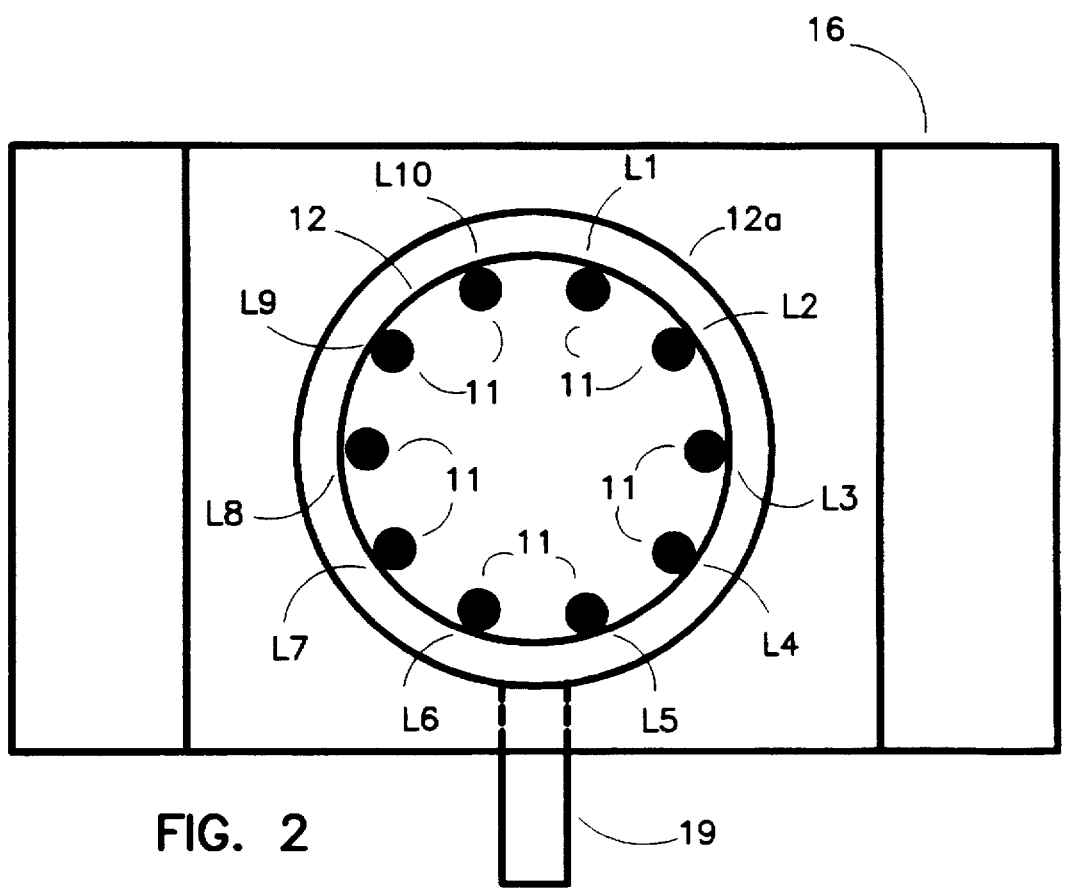
FIG. 2 is a front view of the device for exercising the ciliary muscle of one eye at a time.
Figure 3:
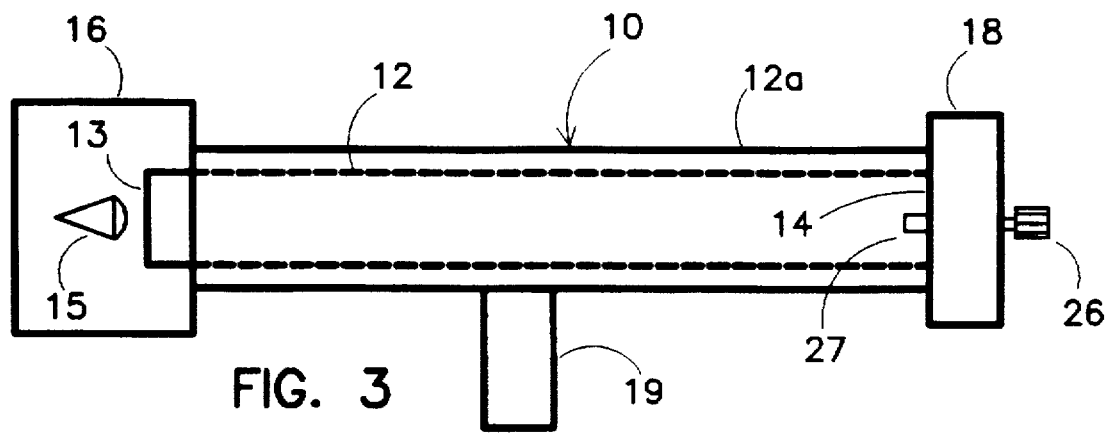
FIG. 3 is an elevated side view of the device for exercising the ciliary muscle of one eye at a time.

Referring to FIG. 1 through 3 the device for exercising the ciliary muscle generally designated 10, has ten light emitting diodes L1, L2, L3, L4, L5, L6, L7, L8, L9, and L10 as light sources 11, disposed and mounted on the inner surface of a first tubular enclosure 12. Said first tubular enclosure 12 has one end open 13 and the other end is closed 14. Said open end 13 is to be located in front of only one eye 15 to be exercised. Said light sources 11 are located at different distances from the open end 13 and aimed toward said open end 13. A shield 16 is located around said first tubular enclosure 12 and adjacent to its open end 13 to cover the eye at rest 17. A second tubular enclosure 12a surrounds said first tubular enclosure 12 providing an space between them for electrical conductors. Handle 19 is used to hold the device in front of eye 15. Casing 18 is used to house the electronic circuitry that powers and controls said light sources 11, and an electric battery.

Figure 7:
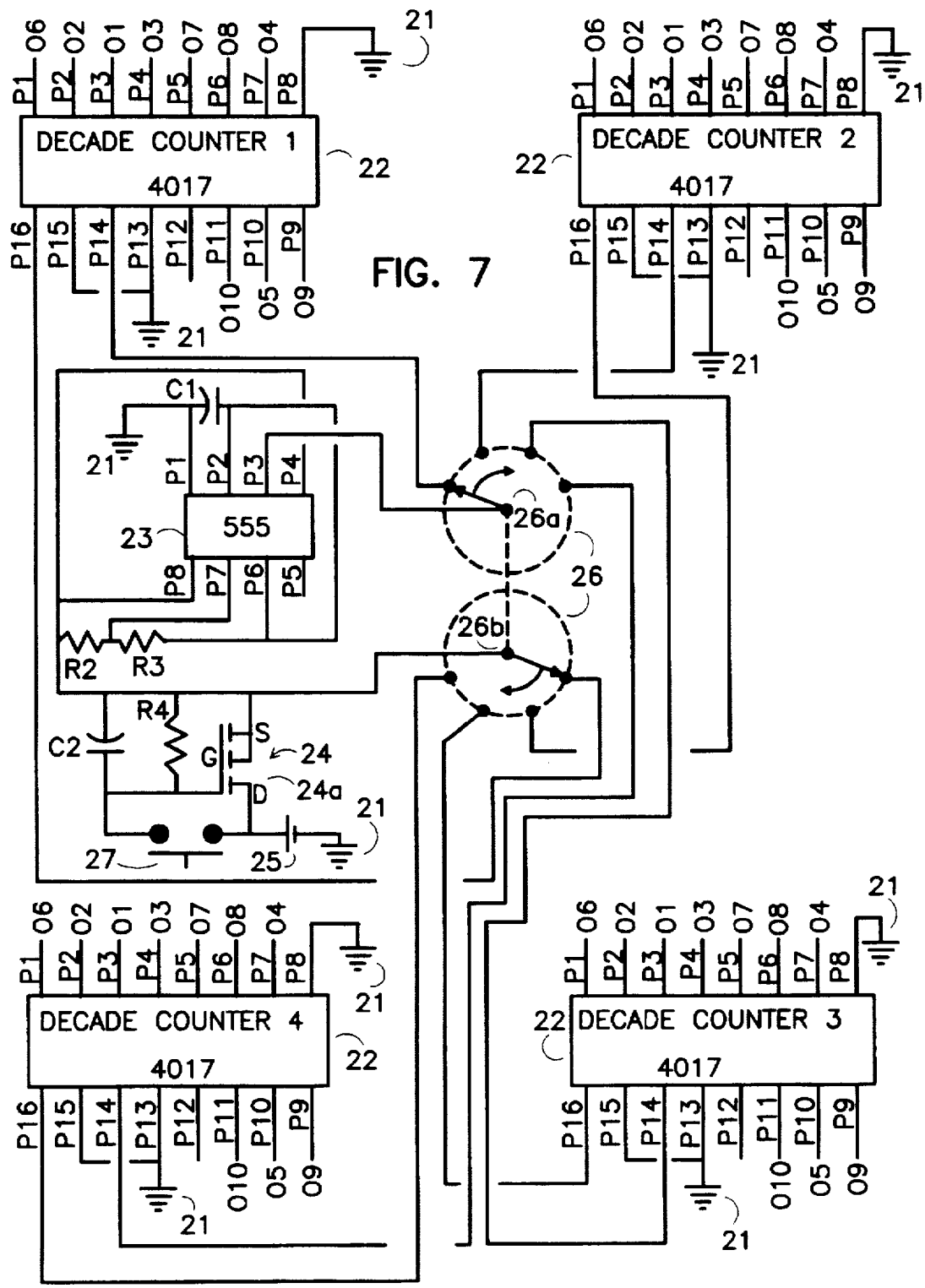
FIGS. 7 and 7A are the schematic diagrams of the electronic circuitry that powers and controls the light sources.
Figure 7A:
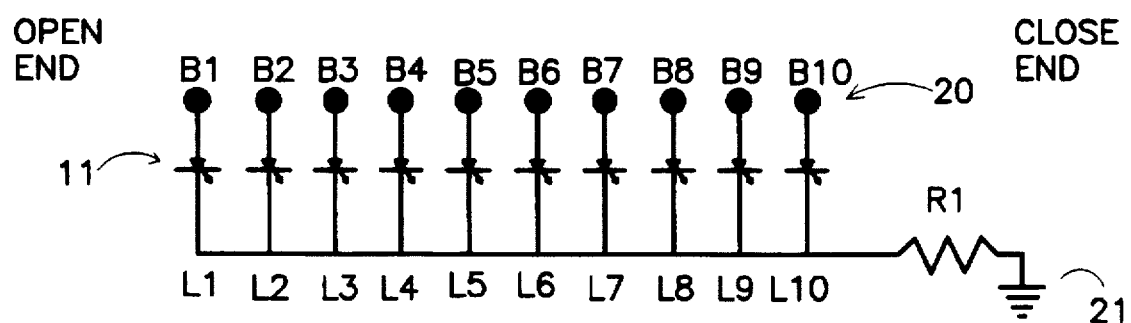

Referring to FIGS. 7 and 7A, light emitting diodes L1, L2, L3, L4, L5, L6, L7, L8, L9, and L10 have their anodes electrically connected to electric conductive buses B1, B2, B3, B4, B5, B6, B7, B8, B9, and B10 respectively. Electric conductive buses B1, B2, B3, B4, B5, B6, B7, B8, B9, and B10 are generally designated 20. Electric paths are provided from the cathodes of all light sources 11 to ground 21. Decade counters typically number 4017 generally designated 22 have ten decoded outputs O1, O2, O3, O4, O5, O6, O7, O8, O9 and O10. When an output turns high the preceding output turns low and remains low until the end of the cycle. Electric paths are provided in said decade counters to count from one to ten and recycle. Electric paths are provided from the outputs of decade counter 1 to buses 20 in accordance with table No. 1, for a squence from the open end 13 to the close end 14 of ten light sources 11. When a light source 11 is turned off the following light source 11 is turned on almost immediately.

TABLE 1

(Decade counter 1)

| Decade counter Output | Bus |
|---|---|
| O1 | B1 |
| O2 | B2 |
| O3 | B3 |
| O4 | B4 |
| O5 | B5 |
| O6 | B6 |
| O7 | B7 |
| O8 | B8 |
| O9 | B9 |
| O10 | B10 |

Electric paths are provided from the outputs of decade counter 2 to buses 20 in accordance with Table No. 2, for a sequence from the close end 14 to the open end 13 of ten light sources 11. When a light source 11 turns off the following light source 11 is turned on almost immediately.

TABLE 2

(Decade counter 2)

| Decade counter Output | Bus |
|---|---|
| O1 | B10 |
| O2 | B9 |
| O3 | B8 |
| O4 | B7 |
| O5 | B6 |
| O6 | B5 |
| O7 | B4 |
| O8 | B3 |
| O9 | B2 |
| O10 | B1 |

Electric paths are provided from the outputs of decade counter 3 to buses 20 in accordance with Table No. 3, for a sequence from the open end 13 to the close end 14 of five light sources 11. When a light source 11 turns off the following light source 11 turns on after a predetermined time delay.

TABLE 3

(Decade counter 3)

| Decade counter Output | Bus |
|---|---|
| O1 | B1 |
| O2 | Not connected |
| O3 | B3 |
| O4 | Not connected |

TABLE 3-continued (Decade counter 3)

| Decade counter Output | Bus |
|---|---|
| O5 | B5 |
| O6 | Not connected |
| O7 | B7 |
| O8 | Not connected |
| O9 | B9 |
| O10 | Not connected |

Electric paths are provided from the outputs of decade counter 4 to buses 20 in accordance with Table No. 4, for a sequence from the close end 14 to the open end 13 of five light sources 11. When a light source 11 turns off the following light source 11 turns on after a predetermined time delay.

TABLE 4

(Decade counter 4)

| Decade counter output | Bus |
|---|---|
| O1 | B10 |
| O2 | Not connected |
| O3 | B8 |
| O4 | Not connected |
| O5 | B6 |
| O6 | Not connected |
| O7 | B4 |
| O8 | Not connected |
| O9 | B2 |
| O10 | Not connected |

Electric paths are provided from pin 8 of all decade counters 22 to ground 21. Electric paths are provided from pin 13 and pin 15 of all decade counter 22 to ground 21, for count recycle operation.

Timer 555 generally designated 23 is used as an oscillator. Frequency of oscillator 23 is adjusted by means of resistors R2, R3 and capacitor C1.

OFF after delay switch 24 uses an N-channel MOSFET transistor typically IRF511 designated 24a. The time delay of said switch 24 is adjusted by means of resistor R4 and capacitor C2.

Battery 25 provides the power for the time delay switch 24, the oscillator 23 and all decade counters 22. Said battery 25 may be of the recharchable type. Means to recharge in-place the recharchable battery may be provided.

Two pole four position rotary selector switch 26 is of the break before make type. Pole 1 is designated 26a and pole 2 is designated 26b. Electric path is provided between pole 1 of said rotary selector switch 26 and the output of said oscillator 23. Electric paths are provided respectively from positions 1 through 4 of pole 1 to pin 14 of decade counters 1 through 4. Electric paths are provided from terminal S of the N-channel MOSFET transistor 24a to pin 14 of said oscillator 23 and to pole 2 of said rotary selector switch 26. Electric paths are provided respectively from position 1 through 4 of pole 2 to pin 16 of decade counters 1 through 4.

When push button 27 is depressed momentarily capacitor C2 is charged through parallel internal impedances of oscillator 23 and that of the decade counter selected through pole 2 of rotary selector switch 26. The N-channel MOSFET transistor 24a becomes conductive energizing oscillator 23 and the decade counter selected by pole 2 of said rotary selector switch 26. The N-channel MOSFET transistor 24a remains conductive until the capacitor C2 discharges through resistor R4 and the internal impedance of said transistor 24a.

A second preferred embodiment

Figure 4:
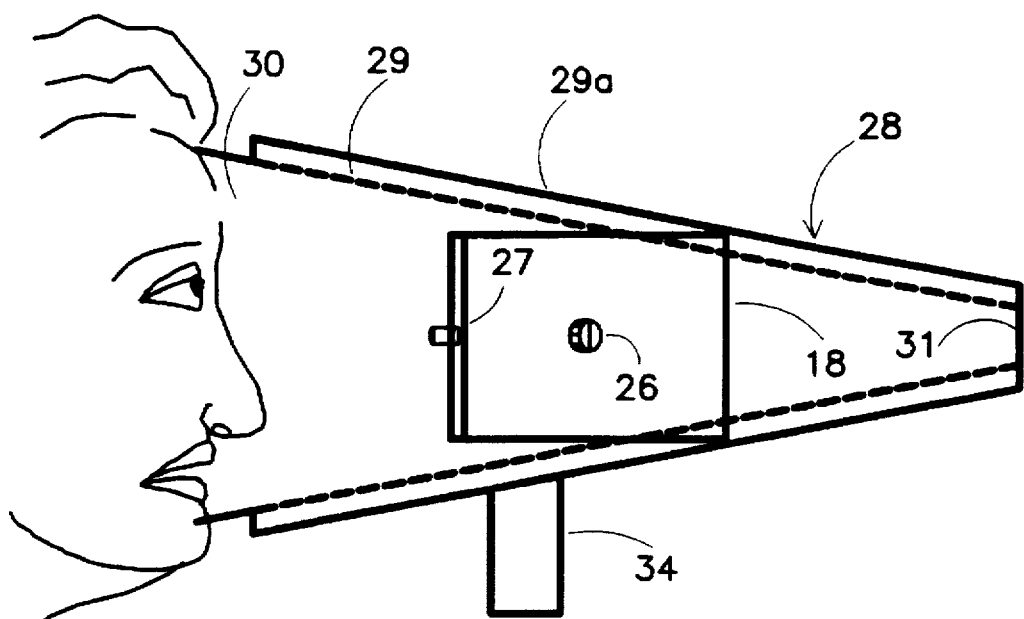
FIG. 4 is an elevated side view of the device for exercising the ciliary muscle of both eyes simultaneously, or one eye at a time.
Figure 5:
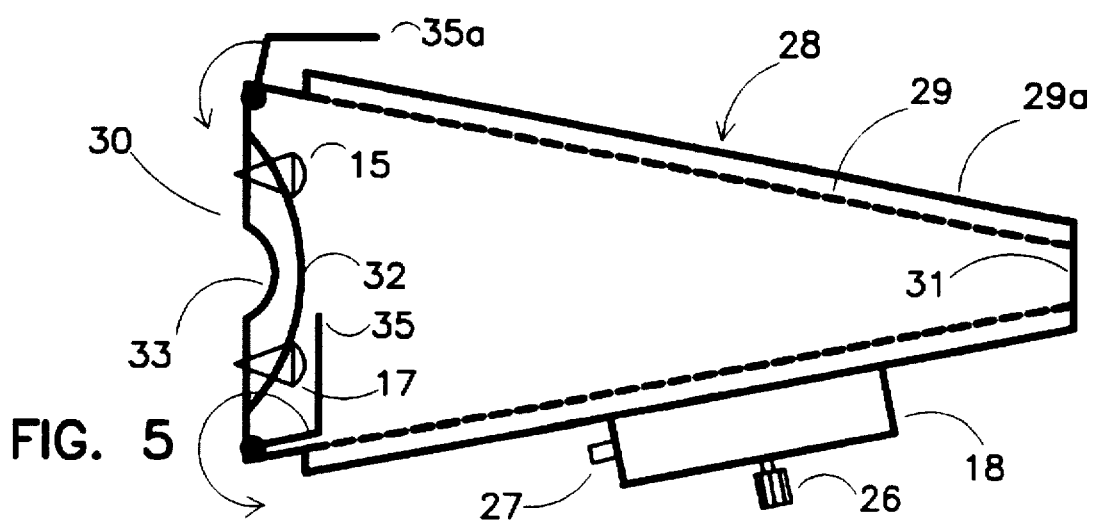
FIG. 5 is a top view of the device for exercising the ciliary muscle of both eyes simultaneously or one eye at a time.
Figure 6:
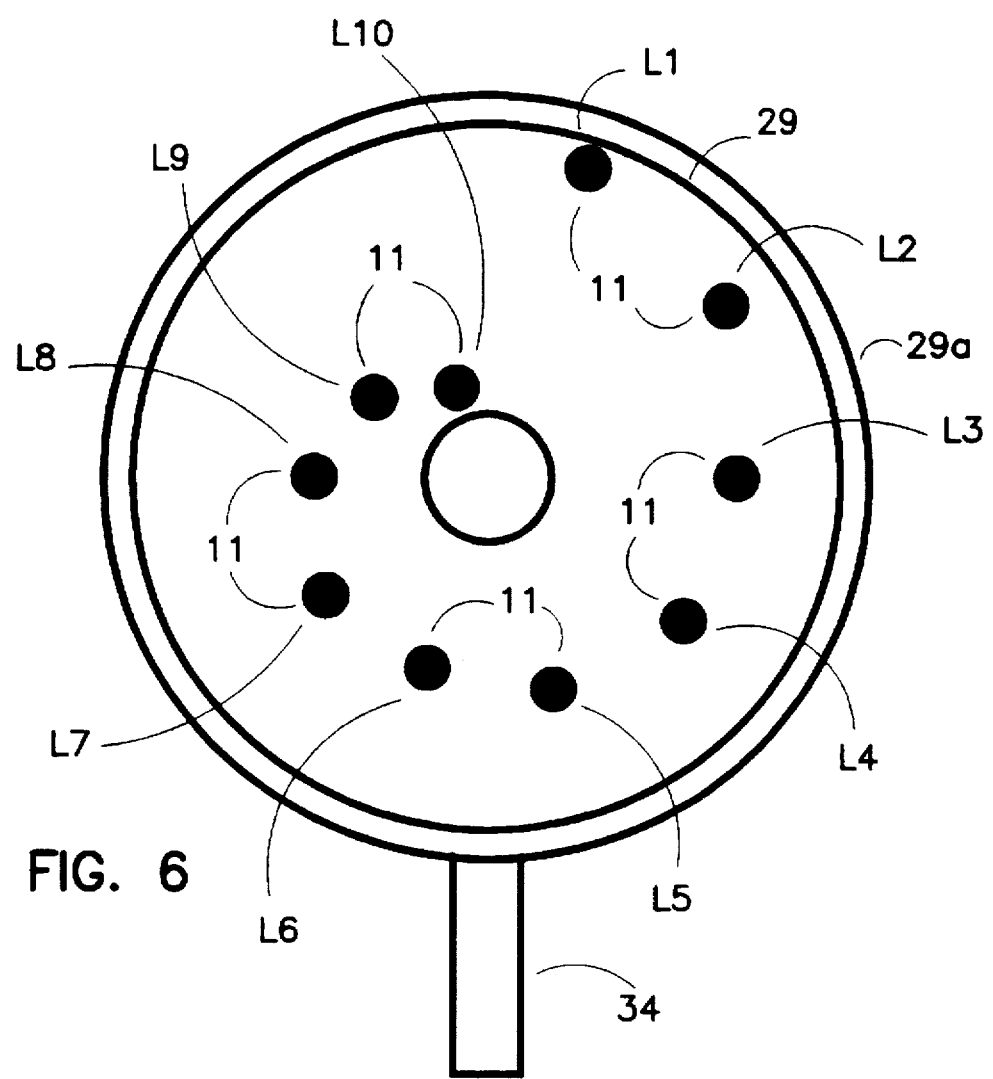
FIG. 6 is a front view of the device for exercising the ciliary muscle of both eyes simultaneously or one eye at a time.

Referring to FIG. 4 through 6 the device for exercising the ciliary muscle generally designated 28, has ten light emitting diodes L1, L2, L3, L4, L5, L6, L7, L8, L9, and L10 as light sources 11, disposed and mounted on the inner surface of a first tubular enclosure 29. Said first tubular enclosure 29 has one end open 30 and the other end is closed 31. Said open end 30 is of sufficient amplitude to allow to be located in front of both eyes to be exercised simultaneously or one at a time. Said light sources 11 are located at different distances from said open end 30 and aimed toward said open end 30. A second tubular enclosure 29a surrounds said first tubular enclosure 29 providing an space betwween them. The space between said first tubular enclosure 29 and second tubular enclosure 29a is used for electrical conductors. The cross section of 29 and 29a diminishes from said open end 30 to said close end 31. The edge of said first tubular enclosure 29 at said open end 30 is shaped to conform with forehead contour 32 and chin contour 33. Handle 34 is used to hold the device in front of the eyes. Casing 18 is used to house the electronic circuitry that powers and controls said light sources 11, and an electric battery.

FIG. 7 and 7A are the schematic diagrams of the electronic circuitry that powers and controls said light sources 11 in accordance with tables 1 through 4.

The present disclosure contains that contained in the appended claims as well as that of the foregoing description. Although the invention has been disclosed in its preferred forms with a certain degree of particularity, it is understood that the invention of the preferred form has been made by way of example, that numerous changes in the details of construction and the combination and arrangement of parts may be resorted to without departing from the spirit and scope of the invention.

What is claimed is:

1. A device for exercising the ciliary muscle comprising in combination:

a first tubular enclosure with one end being open and the other end being closed;

a plurality of light sources disposed and mounted on the inner surface of said first tubular enclosure, at different distances from the open end, and aimed toward the open end;

a second tubular enclosure that surrounds said first tubular enclosure;

an space between said first and second tubular enclosures for electrical conductors;

an electronic circuitry to control said plurality of light sources;

an electric battery;

a casing to house said electronic circuitry and electric battery;

a handle.

2. A devise as set forth in claim 1 wherein said plurality of light sources are turned on and off sequentially in the direction from the open end to the close end of said first tubular enclosure.

3. A device set forth in claim 1 wherein said plurality of light sources are turned on and off sequentially in the direction from the close end to the open end of said first tubular enclosure.

4. A device as set forth in claim 1 wherein said plurality of light sources are turned on and off sequentially with a time delay between the off and on states, in the direction from the open end to the close end of said first tubular enclosure.

5. A device as set forth in claim 1 wherein said plurality of light sources are turned on and off sequentially with a time delay between the off and on states, in the direction from the close end to the open end of said first tubular enclosure.

6. A device as set forth in claim 1 wherein the open end of said first tubular enclosure is of sufficient amplitude to exercise only one eye while the other eye is at rest.

7. A device as set forth in claim 6 wherein a shield is provide to cover the eye at rest.

8. A device as set forth in claim 1 wherein the open end of said first tubular enclosure is of sufficient amplitude to exercise both eyes simultaneously or one eye at a time.

9. A device as set forth in claim 8 wherein the amplitude of the cross section of said first and second tubular enclosures diminishes from the open end to the close end.

10. A device as set forth at least in claim 9 wherein the edge of the open end of said first tubular enclosure is shaped to conform with the contours of forehead and chin.

11. A device as set forth at least in claim 9 wherein two movable shields are provided to cover one eye at a time while the other eye is exercised.

* * * * *